United States Patent
Kassab

(10) Patent No.: US 10,245,049 B2
(45) Date of Patent: Apr. 2, 2019

(54) THROMBUS REMOVAL SYSTEMS AND DEVICES AND METHODS OF USING THE SAME

(75) Inventor: Ghassan S. Kassab, Zionsville, IN (US)

(73) Assignee: CVDevices, LLC, San Diego, CA (US)

( * ) Notice: Subject to any disclaimer, the term of this patent is extended or adjusted under 35 U.S.C. 154(b) by 111 days.

(21) Appl. No.: 13/491,754

(22) Filed: Jun. 8, 2012

(65) Prior Publication Data
US 2012/0316599 A1    Dec. 13, 2012

Related U.S. Application Data

(60) Provisional application No. 61/494,561, filed on Jun. 8, 2011.

(51) Int. Cl.
*A61B 17/22*    (2006.01)

(52) U.S. Cl.
CPC .... *A61B 17/22* (2013.01); *A61B 2017/22044* (2013.01); *A61B 2017/22054* (2013.01); *A61B 2017/22067* (2013.01); *A61B 2017/22084* (2013.01)

(58) Field of Classification Search
CPC ........ A61B 17/12109; A61B 17/12022; A61B 17/12027; A61B 17/12031; A61B 17/12036; A61B 17/1204; A61B 17/12045; A61B 17/12136; A61B 17/22; A61B 2017/12127; A61B 2017/22051; A61B 2017/22054; A61B 2017/22055; A61B 17/3207; A61B 2017/320716; A61F 2/2436; A61F 2/2433; A61F 2/01; A61M 29/00; A61M 29/02; A61M 25/10; A61M 25/1011

USPC .................. 606/113, 114, 127, 200
See application file for complete search history.

(56) References Cited

U.S. PATENT DOCUMENTS

| | | | | |
|---|---|---|---|---|
| 4,794,928 | A | * | 1/1989 | Kletschka ........ A61B 17/12109 604/101.01 |
| 5,135,484 | A | * | 8/1992 | Wright .................. A61B 17/22 604/101.03 |
| 5,419,763 | A | * | 5/1995 | Hildebrand ........ A61M 25/1011 604/101.03 |

(Continued)

*Primary Examiner* — Eric Rosen
*Assistant Examiner* — Chima Igboko
(74) *Attorney, Agent, or Firm* — Reichel Stohry LLP; Mark C. Reichel; Natalie J. Dean

(57) ABSTRACT

Thrombus removal systems and devices and methods of using the same. In an exemplary embodiment of a thrombus removal system of the present disclosure, the thrombus removal system comprises an umbrella catheter comprising an umbrella catheter tube and an umbrella positioned at least partially within the umbrella catheter tube when in a compressed configuration and positioned external to the umbrella catheter tube when in a deployed configuration, and a balloon catheter configured to fit around at least part of the umbrella catheter, the balloon catheter comprising a balloon catheter tube and a balloon coupled thereto, the balloon capable of inflation within a lumen of a mammalian vessel to substantially or completely occlude the lumen of the mammalian vessel, wherein the thrombus removal system is configured to disrupt and/or dissolve and remove at least a portion of a thrombus positioned within the lumen of the mammalian vessel.

18 Claims, 11 Drawing Sheets

(56) References Cited

U.S. PATENT DOCUMENTS

| | | | | |
|---|---|---|---|---|
| 5,462,529 | A * | 10/1995 | Simpson | A61B 17/320758 604/101.04 |
| 5,549,626 | A * | 8/1996 | Miller | A61F 2/01 606/191 |
| 5,584,803 | A * | 12/1996 | Stevens et al. | 604/6.16 |
| 5,941,896 | A * | 8/1999 | Kerr | A61F 2/01 606/192 |
| 5,954,745 | A * | 9/1999 | Gertler et al. | 606/200 |
| 6,485,500 | B1 * | 11/2002 | Kokish | A61M 25/104 604/101.01 |
| 6,485,501 | B1 * | 11/2002 | Green | 606/200 |
| 6,793,668 | B1 * | 9/2004 | Fisher | 606/200 |
| 7,166,120 | B2 * | 1/2007 | Kusleika | A61F 2/013 128/898 |
| 7,585,321 | B2 * | 9/2009 | Cribier | 623/2.14 |
| 2001/0041865 | A1 * | 11/2001 | Delaney | A61B 5/14539 604/102.01 |
| 2001/0051784 | A1 * | 12/2001 | Brisken | A61B 17/22012 604/22 |
| 2002/0188276 | A1 * | 12/2002 | Evans | A61B 17/22 604/509 |
| 2003/0163158 | A1 * | 8/2003 | White | 606/200 |
| 2003/0187494 | A1 * | 10/2003 | Loaldi | 623/1.11 |
| 2003/0195537 | A1 * | 10/2003 | Dubrul et al. | 606/159 |
| 2004/0019348 | A1 * | 1/2004 | Stevens et al. | 606/34 |
| 2004/0117032 | A1 * | 6/2004 | Roth | 623/23.72 |
| 2004/0127935 | A1 * | 7/2004 | VanTassel et al. | 606/200 |
| 2004/0220609 | A1 * | 11/2004 | Douk et al. | 606/200 |
| 2005/0033172 | A1 * | 2/2005 | Dubrul et al. | 600/439 |
| 2005/0043756 | A1 * | 2/2005 | Lavelle et al. | 606/200 |
| 2005/0149110 | A1 * | 7/2005 | Wholey et al. | 606/200 |
| 2005/0192620 | A1 * | 9/2005 | Cully et al. | 606/200 |
| 2005/0222583 | A1 * | 10/2005 | Cano et al. | 606/108 |
| 2005/0240146 | A1 * | 10/2005 | Nash et al. | 604/35 |
| 2006/0030814 | A1 * | 2/2006 | Valencia et al. | 604/93.01 |
| 2006/0100662 | A1 * | 5/2006 | Daniel et al. | 606/200 |
| 2006/0241680 | A1 * | 10/2006 | Johnson et al. | 606/200 |
| 2007/0010806 | A1 * | 1/2007 | Malecki et al. | 606/27 |
| 2007/0078485 | A1 * | 4/2007 | Deem et al. | 606/213 |
| 2007/0123932 | A1 * | 5/2007 | Gray et al. | 606/200 |
| 2007/0197962 | A1 * | 8/2007 | Morikawa | 604/96.01 |
| 2007/0282303 | A1 * | 12/2007 | Nash et al. | 604/510 |
| 2008/0058860 | A1 * | 3/2008 | Demond et al. | 606/200 |
| 2008/0119889 | A1 * | 5/2008 | Kusleika | 606/200 |
| 2008/0215036 | A1 * | 9/2008 | Vogel | A61B 17/12131 604/514 |
| 2009/0228036 | A1 * | 9/2009 | Cano et al. | 606/200 |
| 2009/0287166 | A1 * | 11/2009 | Dang | 604/265 |
| 2010/0004607 | A1 * | 1/2010 | Wilson et al. | 604/266 |
| 2010/0114113 | A1 * | 5/2010 | Dubrul et al. | 606/127 |

* cited by examiner

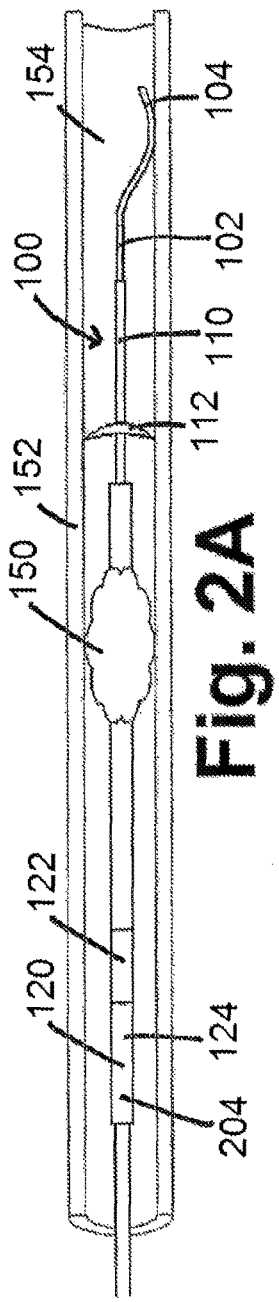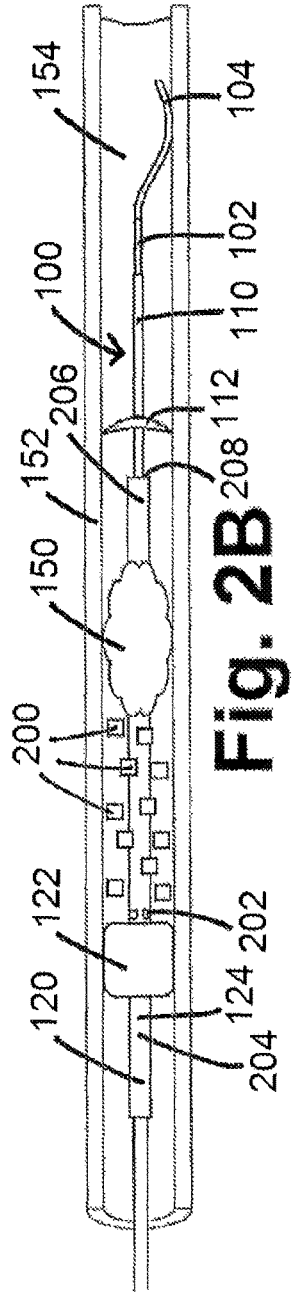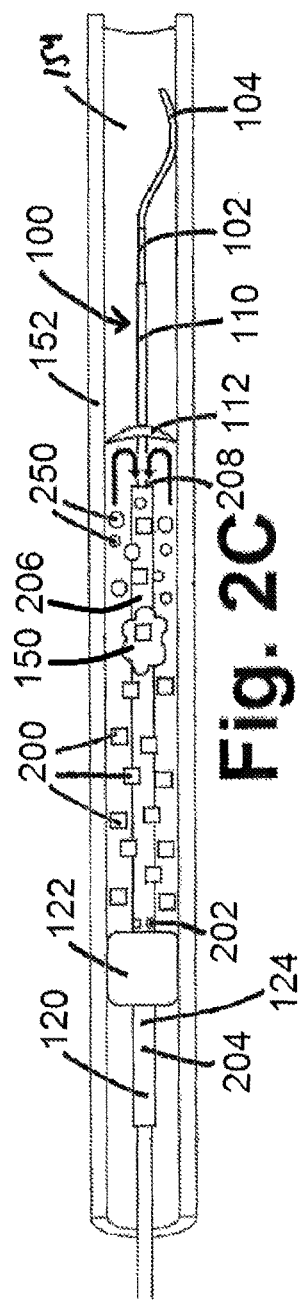

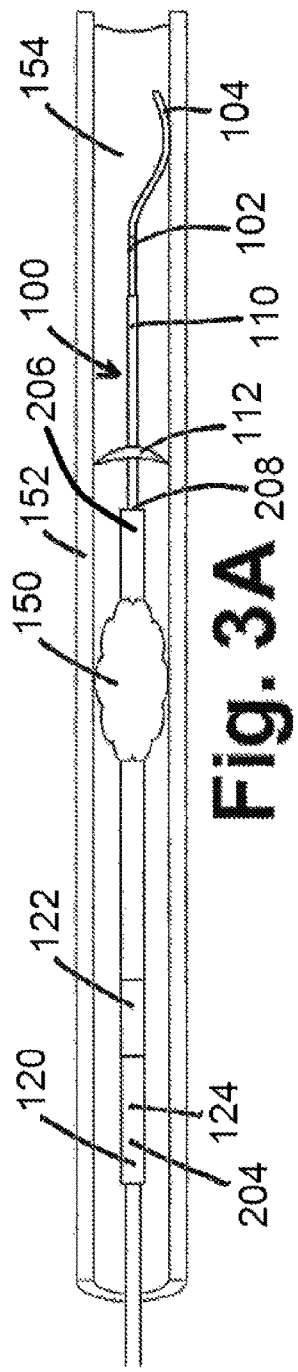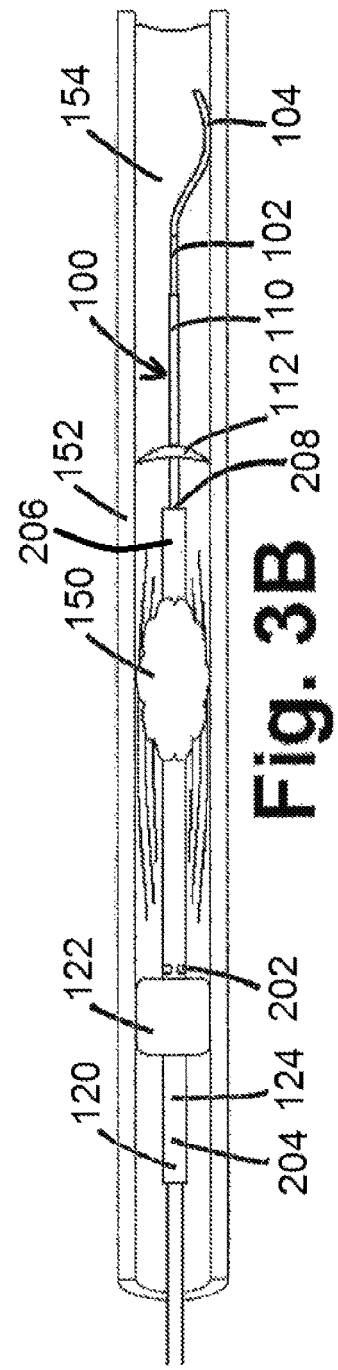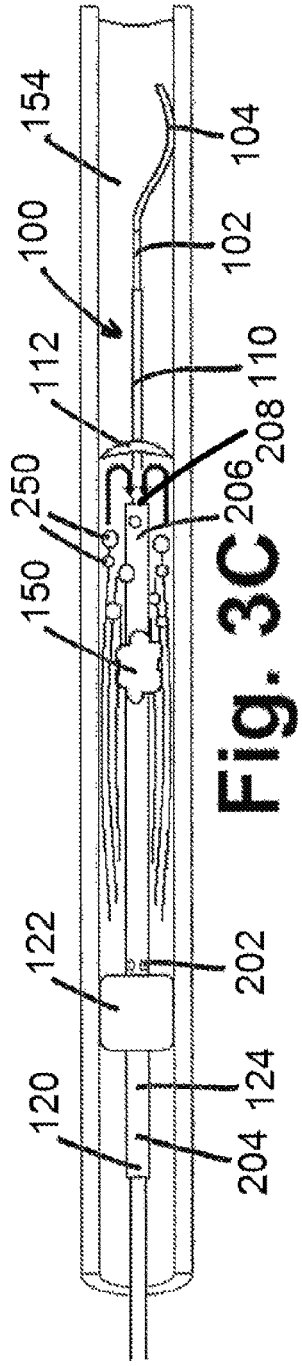

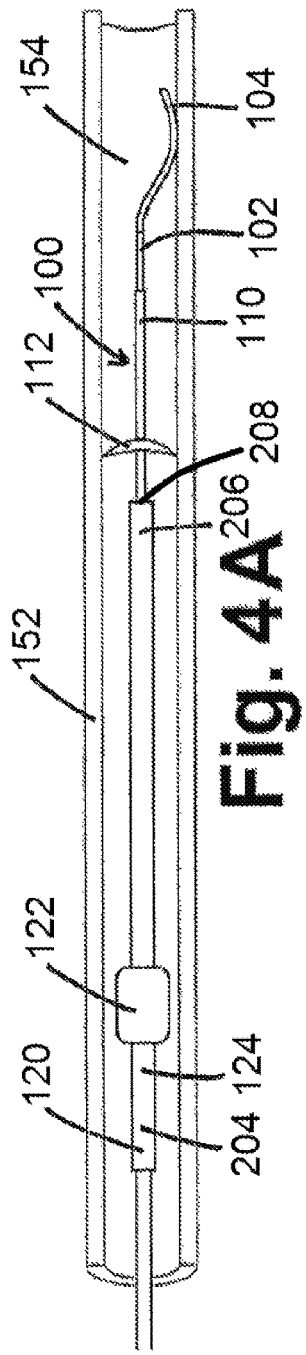
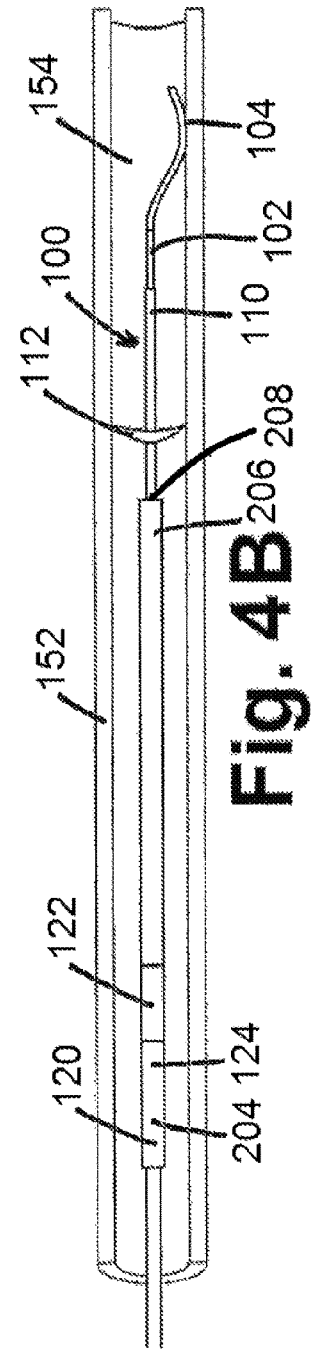
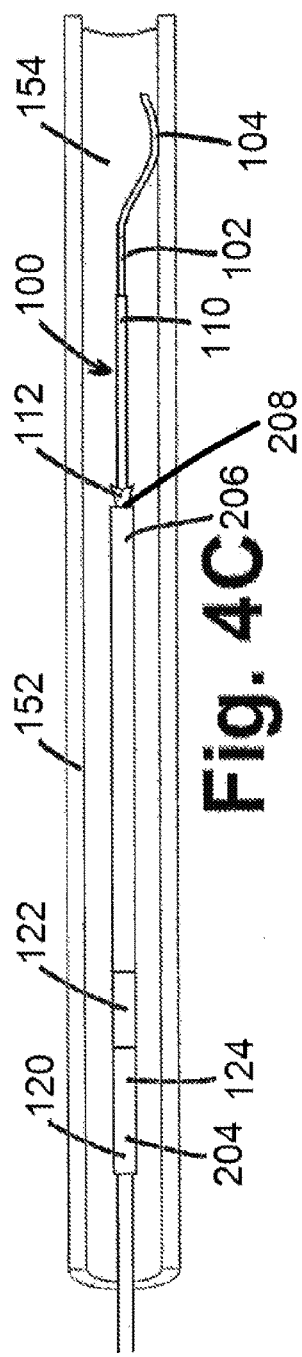

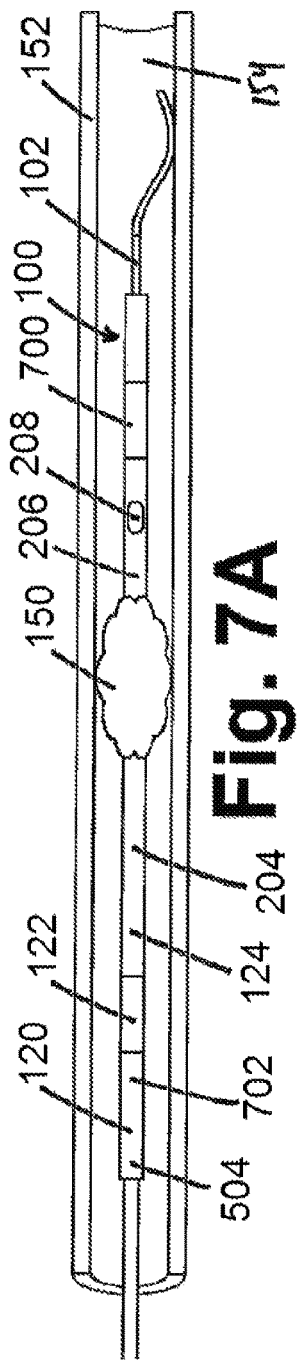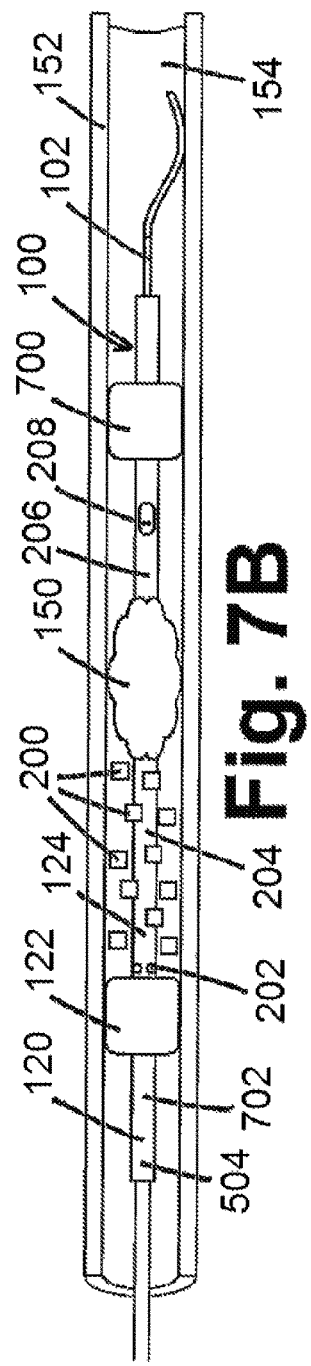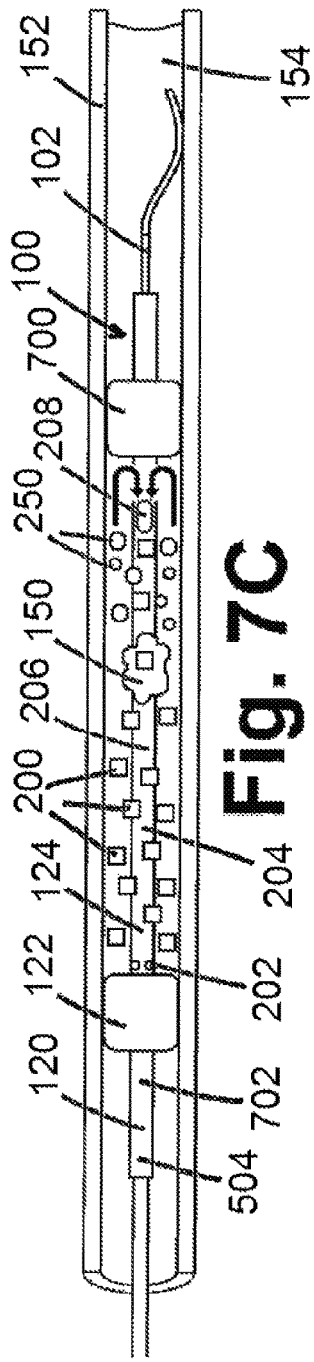

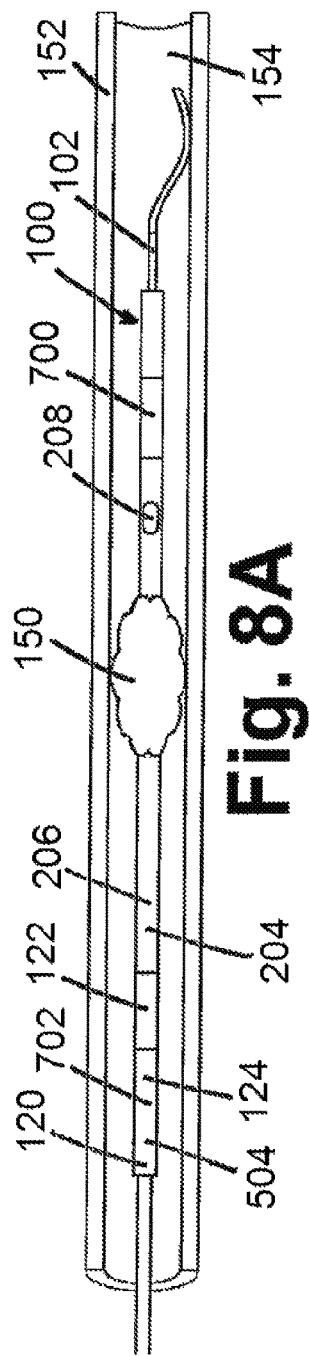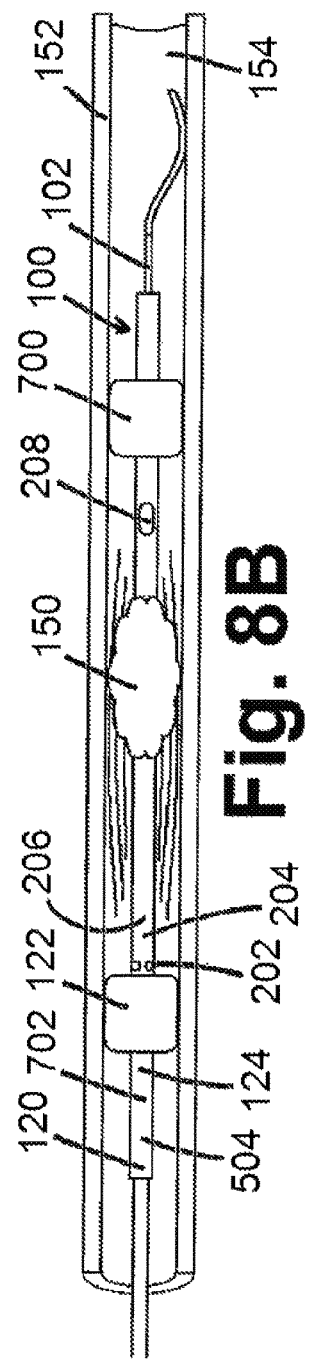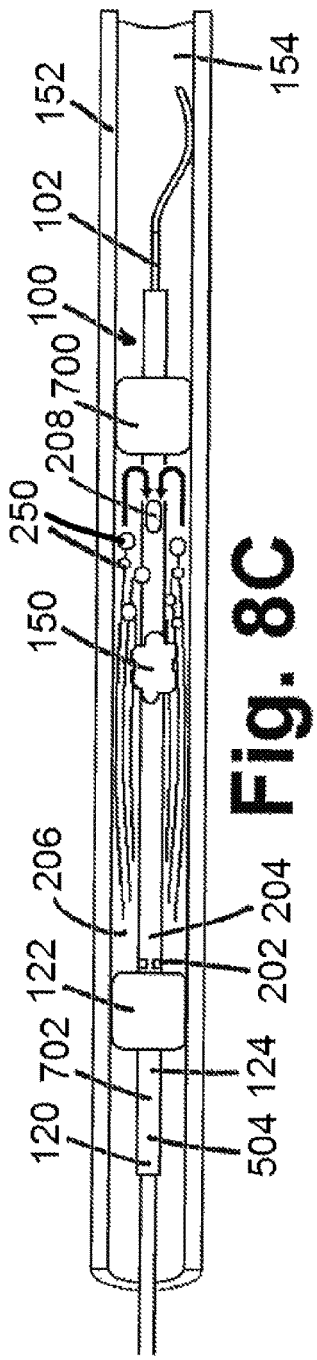

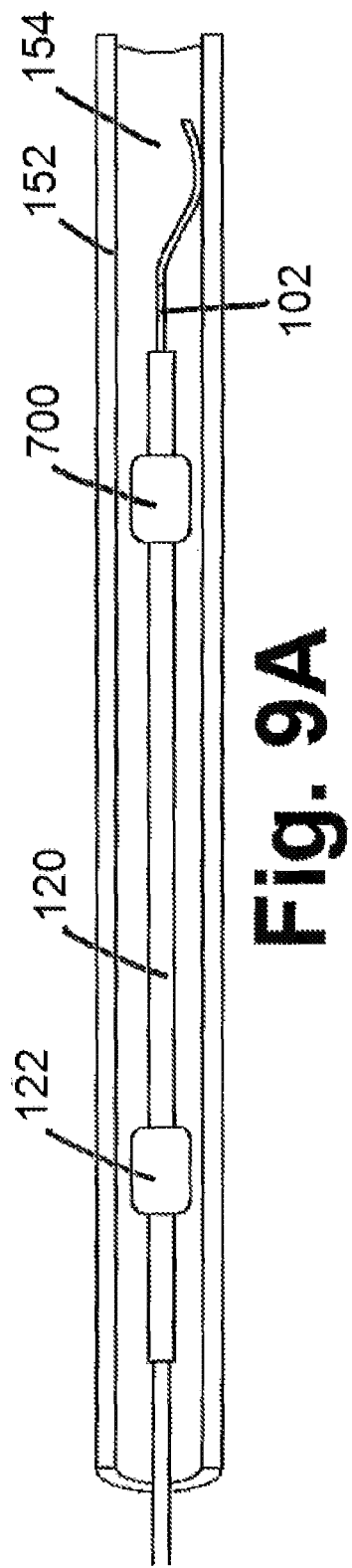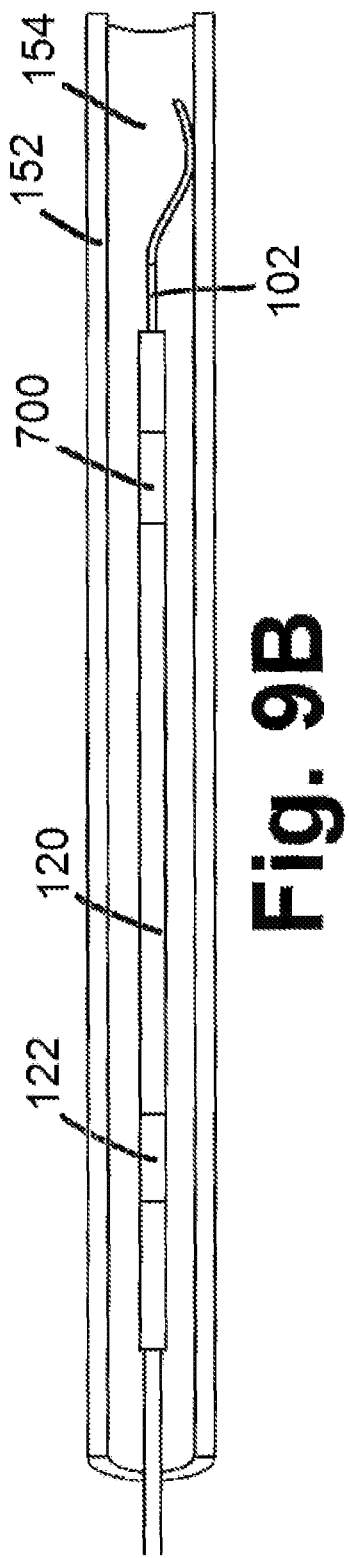

THROMBUS REMOVAL SYSTEMS AND DEVICES AND METHODS OF USING THE SAME

PRIORITY

The present application is related to, and claims the priority benefit of, U.S. Provisional Patent Application Ser. No. 61/494,561, filed Jun. 8, 2011, the contents of which are incorporated by reference in their entirety into this disclosure.

BACKGROUND

Thrombogenesis, which involves the localized accumulation of blood elements on an injured vessel wall, can cause heart attacks and strokes. Although a thrombus is initially composed of platelets and fibrin that serve to limit bleeding, excessive thrombus growth can lead to thrombosis that obstructs blood vessels and hence can produce ischemia in vascular beds.

In patients at risk of thrombosis, conventional drug treatments (such as aspirin, heparin, and warfarin, for example) are used to slow thrombus growth. However, such treatments have the risk of bleeding complications that can be serious and sometimes fatal. For patients that develop a thrombus, there are approaches known in the art for retrieval of the thrombus (such as catheters and balloons) as well as chemical approaches to dissolve the thrombus (such as tissue plasminogen activators or plasmin). The chemicals, however, are not localized to the thrombus and can circulate through the patient's blood and cause bleeding. Hence, there is a need for localization of thrombus dissolution either chemically or physically and its removal without affecting the rest of the cardiovascular system.

BRIEF SUMMARY

The disclosure of the present application provides various thrombus removal systems and devices and methods of using the same.

In an exemplary embodiment of a thrombus removal system of the present disclosure, the thrombus removal system comprises an umbrella catheter comprising an umbrella catheter tube and an umbrella positioned at least partially within the umbrella catheter tube when in a compressed configuration and positioned external to the umbrella catheter tube when in a deployed configuration, and a balloon catheter configured to fit around at least part of the umbrella catheter, the balloon catheter comprising a balloon catheter tube and a balloon coupled thereto, the balloon capable of inflation within a lumen of a mammalian vessel to substantially or completely occlude the lumen of the mammalian vessel, the thrombus removal system configured to disrupt and/or dissolve and remove at least a portion of a thrombus positioned within the lumen of the mammalian vessel. In another embodiment, at least part of the umbrella catheter is configured to fit around a guidewire. In yet another embodiment, the system further comprises a guidewire having a distal end, the guidewire configured to puncture the thrombus and further configured to allow at least part of the umbrella catheter to fit around the guidewire. In an additional embodiment, the umbrella is configured to at least substantially occlude the lumen of the mammalian vessel when in the deployed configuration.

In an exemplary embodiment of a thrombus removal system of the present disclosure, wherein the umbrella is configured to at allow fluid to pass therethrough but prevent at least a portion of the thrombus from passing therethrough when in the deployed configuration. In an additional embodiment, the system is configured to introduce one or more chemical agents into the lumen of the mammalian vessel, the one or more chemical agents capable of disrupting and/or dissolving at least a portion of the thrombus. In yet an additional embodiment, the one or more chemical agents are selected from the group consisting of a tissue plasminogen activator, plasmin and thrombin.

In an exemplary embodiment of a thrombus removal system of the present disclosure, the balloon catheter tube further defines one or more apertures therein, the one or more apertures configured to allow a fluid and/or a substance to pass therethrough from a first balloon catheter lumen defined within the balloon catheter tube. In another embodiment, the balloon catheter tube is configured so that one or more chemical agents can be introduced through the first balloon catheter lumen, through the one or more apertures, and into the lumen of the mammalian vessel. In another embodiment, the balloon catheter tube further defines a distal tube aperture in communication with a second balloon catheter lumen, wherein a fluid and/or a substance from within the lumen of the mammalian vessel can enter second balloon catheter lumen through the distal tube aperture when suction is applied through the second balloon catheter lumen. In an additional embodiment, the balloon catheter tube further defines a distal tube aperture in communication with a second balloon catheter lumen, wherein at least a portion of the thrombus from within the lumen of the mammalian vessel can enter second balloon catheter lumen through the distal tube aperture when suction is applied through the second balloon catheter lumen to remove at least a portion of the thrombus. In yet an additional embodiment, the balloon catheter tube is configured so that a fluid can be introduced through the first balloon catheter lumen, through the one or more apertures, and into the lumen of the mammalian vessel to flush the lumen of the mammalian vessel.

In an exemplary embodiment of a thrombus removal system of the present disclosure, the system is configured to introduce one or more disruptive oscillations into the lumen of the mammalian vessel, the one or more disruptive oscillations capable of disrupting at least a portion of the thrombus. In an additional embodiment, the one or more disruptive oscillations are introduced via ultrasound through one or more of the balloon catheter and the umbrella catheter. In yet an additional embodiment, the balloon is capable of inflation and deflation by way of an inflation/deflation lumen defined within the balloon catheter tube. In another embodiment, the system further comprises an inflation/deflation source in communication with the inflation/deflation lumen, the inflation/deflation source capable of inflating and/or deflating balloon by way of a gas and/or a liquid from the inflation/deflation source.

In an exemplary embodiment of a thrombus removal system of the present disclosure, the system further comprises a substance source in communication with a first balloon catheter lumen defined within the balloon catheter tube, the substance source capable of introducing one or more chemical agents and/or or a fluid from the substance source, through the first balloon catheter lumen, through one or more apertures defined within the balloon catheter tube, and into the lumen of the mammalian vessel. In an additional embodiment, the system further comprises a suction source in communication with a second balloon catheter lumen defined within the balloon catheter tube, the suction source capable of removing fluid and/or a particulate from the lumen of the mammalian vessel during operation of the suction source.

In an exemplary embodiment of a thrombus removal system of the present disclosure, the system comprises a guidewire having a distal end, the guidewire configured to puncture a thrombus positioned within a lumen of a mammalian vessel, an umbrella catheter configured to fit around at least part of the guidewire, the umbrella catheter comprising an umbrella catheter tube and an umbrella positioned at least partially within the umbrella catheter tube when in a compressed configuration and positioned external to the umbrella catheter tube when in a deployed configuration, a balloon catheter configured to fit around at least part of the umbrella catheter, the balloon catheter comprising a balloon catheter tube and a balloon coupled thereto, the balloon capable of inflation within a lumen of a mammalian vessel to substantially or completely occlude the lumen of the mammalian vessel, the balloon catheter defining a first lumen, a second lumen, and a third lumen therethrough, the first lumen in communication with one or more apertures defined within the balloon catheter tube, the second lumen in communication with a distal tube aperture, and the third lumen in communication with the balloon, the thrombus removal system configured to disrupt and/or dissolve and remove at least a portion of the thrombus from within the lumen of the mammalian vessel by way introducing one or more chemical agents and/or one or more disruptive oscillations into the lumen of the vessel, the one or more chemical agents and/or one or more disruptive oscillations capable of disrupting and/or dissolving at least a portion of the thrombus.

In an exemplary embodiment of a thrombus removal system of the present disclosure, the system comprises a balloon catheter optionally configured to fit around at least part of an umbrella catheter, the balloon catheter comprising a balloon catheter tube and a first balloon and a second balloon coupled thereto, the first balloon and the second balloon capable of inflation within a lumen of a mammalian vessel to substantially or completely occlude the lumen of the mammalian vessel, the thrombus removal system configured to disrupt and/or dissolve and remove at least a portion of a thrombus positioned within the lumen of the mammalian vessel. In another embodiment, at least part of the umbrella catheter is configured to fit around a guidewire. In another embodiment, the system further comprises a guidewire having a distal end, the guidewire configured to puncture the thrombus and further configured to allow at least part of the balloon catheter to fit around the guidewire.

In an exemplary embodiment of a thrombus removal system of the present disclosure, the system is configured to introduce one or more chemical agents into the lumen of the mammalian vessel, the one or more chemical agents capable of disrupting and/or dissolving at least a portion of the thrombus. In an additional embodiment, the one or more chemical agents are selected from the group consisting of a tissue plasminogen activator, plasmin and thrombin. In yet an additional embodiment, the balloon catheter tube further defines one or more apertures therein, the one or more apertures configured to allow a fluid and/or a substance to pass therethrough from a first balloon catheter lumen defined within the balloon catheter tube. In another embodiment, the balloon catheter tube is configured so that one or more chemical agents can be introduced through the first balloon catheter lumen, through the one or more apertures, and into the lumen of the mammalian vessel.

In an exemplary embodiment of a thrombus removal system of the present disclosure, the balloon catheter tube further defines a removal aperture in communication with a second balloon catheter lumen, wherein a fluid and/or a substance from within the lumen of the mammalian vessel can enter second balloon catheter lumen through the removal aperture when suction is applied through the second balloon catheter lumen. In another embodiment, the balloon catheter tube further defines a removal aperture in communication with a second balloon catheter lumen, wherein at least a portion of the thrombus from within the lumen of the mammalian vessel can enter second balloon catheter lumen through the removal aperture when suction is applied through the second balloon catheter lumen to remove at least a portion of the thrombus. In yet another embodiment, the balloon catheter tube is configured so that a fluid can be introduced through the first balloon catheter lumen, through the one or more apertures, and into the lumen of the mammalian vessel to flush the lumen of the mammalian vessel. In an additional embodiment, the system is configured to introduce one or more disruptive oscillations into the lumen of the mammalian vessel, the one or more disruptive oscillations capable of disrupting at least a portion of the thrombus. In yet an additional embodiment, the one or more disruptive oscillations are introduced via ultrasound through the balloon catheter.

In an exemplary embodiment of a thrombus removal system of the present disclosure, the first balloon and the second balloon are capable of inflation and deflation by way of at least one inflation/deflation lumen defined within the balloon catheter tube. In an additional embodiment, the system further comprises an inflation/deflation source in communication with the at least one inflation/deflation lumen, the inflation/deflation source capable of inflating and/or deflating the first balloon and the second balloon by way of a gas and/or a liquid from the inflation/deflation source. In yet an additional embodiment, the system further comprises a substance source in communication with a first balloon catheter lumen defined within the balloon catheter tube, the substance source capable of introducing one or more chemical agents and/or or a fluid from the substance source, through the first balloon catheter lumen, through one or more apertures defined within the balloon catheter tube, and into the lumen of the mammalian vessel. In another embodiment, the system further comprises a suction source in communication with a second balloon catheter lumen defined within the balloon catheter tube, the suction source capable of removing fluid and/or a particulate In an exemplary embodiment of a method of removing a thrombus from a lumen of a mammalian vessel of the present disclosure, the method comprises the steps of inserting a guidewire into a lumen of a mammalian vessel through a thrombus present therein, inserting an umbrella catheter through the thrombus around at least part of the guidewire, inserting a balloon catheter through the thrombus around at least part of the umbrella catheter, deploying an umbrella of the umbrella catheter to at least substantially occlude the lumen of the mammalian vessel distal to the thrombus or to at least substantially prevent a portion of the thrombus from passing through the umbrella, inflating a balloon of the balloon catheter to at least substantially occlude the lumen of the mammalian vessel proximal to the thrombus, operating one or more of the umbrella catheter and/or the balloon catheter to disrupt and/or dissolve the thrombus, and applying suction through the balloon catheter to remove at least part of the disrupted thrombus from the lumen of the mammalian vessel. In another embodiment, the step of operating one or more of the umbrella catheter and/or the balloon catheter comprises introducing one or more chemical agents through the balloon catheter into the lumen of the mammalian vessel to disrupt and/or dissolve the thrombus. In yet another embodiment, the step of operating one or more of the umbrella catheter and/or the balloon catheter comprises introducing one or more disruptive oscillations therethrough to disrupt the thrombus. In an additional embodiment, the method further comprises the steps of deflating the balloon and inverting the umbrella so that the umbrella can be positioned at least partially within a distal aperture of the balloon catheter, and removing the guidewire, the umbrella catheter, and the balloon catheter from the lumen of the mammalian vessel.

In an exemplary embodiment of a method of removing a thrombus from a lumen of a mammalian vessel of the present disclosure, the method comprises the steps of inserting a guidewire into a lumen of a mammalian vessel through a thrombus present therein, inserting a balloon catheter through the thrombus around at least part of the guidewire, inflating a first balloon of the balloon catheter to at least substantially occlude the lumen of the mammalian vessel proximal to the thrombus and inflating a second balloon of the balloon catheter to at least substantially occlude the lumen of the mammalian vessel distal to the thrombus, operating the balloon catheter to disrupt and/or dissolve the thrombus, and applying suction through the balloon catheter to remove at least part of the disrupted thrombus from the lumen of the mammalian vessel. In another embodiment, the step of operating the balloon catheter comprises introducing one or more chemical agents through the balloon catheter into the lumen of the mammalian vessel to disrupt and/or dissolve the thrombus. In another embodiment, the step of operating the balloon catheter comprises introducing one or more disruptive oscillations therethrough to disrupt the thrombus. In an additional embodiment, the method further comprising the steps of deflating the first balloon and the second balloon, and removing the guidewire and the balloon catheter from the lumen of the mammalian vessel.

In an exemplary embodiment of a thrombus removal system of the present disclosure, the thrombus removal system comprises a balloon catheter comprising a balloon catheter tube and a first balloon coupled thereto, the first balloon capable of inflation within a lumen of a mammalian vessel to substantially or completely occlude the lumen of the mammalian vessel, and a second occlusion element configured to at least substantially occlude the lumen of the mammalian vessel, wherein the thrombus removal system is configured to disrupt and/or dissolve and remove at least a portion of a thrombus positioned within the lumen of the mammalian vessel. In another embodiment, the second occlusion element comprises an umbrella catheter comprising an umbrella catheter tube and an umbrella positioned at least partially within the umbrella catheter tube when in a compressed configuration and positioned external to the umbrella catheter tube when in a deployed configuration, wherein the umbrella is configured to at least substantially occlude the lumen of the mammalian vessel when in the deployed configuration, and wherein the balloon catheter is configured to fit around at least part of the umbrella catheter. In yet another embodiment, the thrombus removal system further comprises a guidewire having a distal end, the guidewire configured to puncture the thrombus, wherein at least part of the umbrella catheter is configured to fit around the guidewire. In an additional embodiment, the umbrella is configured to at allow fluid to pass therethrough but prevent at least a portion of the thrombus from passing therethrough when in the deployed configuration. In an exemplary embodiment of a thrombus removal system of the present disclosure, when the first balloon is positioned proximal to the thrombus and inflated to at least substantially occlude the lumen of the mammalian vessel and wherein when the umbrella is positioned distal to the thrombus and operated to at least substantially occlude the lumen of the mammalian vessel, operation of one or more of the umbrella catheter and/or the balloon catheter can disrupt and/or dissolve the thrombus, and use of suction through the balloon catheter can facilitate removal of at least part of the disrupted thrombus from the lumen of the mammalian vessel. In an additional embodiment, the first balloon is capable of inflation and deflation by way of an inflation/deflation lumen defined within the balloon catheter tube.

In an exemplary embodiment of a thrombus removal system of the present disclosure, the second occlusion element comprises a second balloon coupled to the balloon catheter tube, the second balloon capable of inflation within the lumen of the mammalian vessel to substantially or completely occlude the lumen of the mammalian vessel, and wherein the first balloon and the second balloon are capable of inflation and deflation by way of at least one inflation/deflation lumen defined within the balloon catheter tube. In another embodiment, when the first balloon is positioned proximal to the thrombus and inflated to at least substantially occlude the lumen of the mammalian vessel and wherein when the second balloon is positioned distal to the thrombus and inflated to at least substantially occlude the lumen of the mammalian vessel, operation of the balloon catheter can disrupt and/or dissolve the thrombus, and use of suction through the balloon catheter can facilitate removal of at least part of the disrupted thrombus from the lumen of the mammalian vessel. In yet another embodiment, the system is configured to introduce one or more chemical agents into the lumen of the mammalian vessel, the one or more chemical agents capable of disrupting and/or dissolving at least a portion of the thrombus. In an additional embodiment, the balloon catheter tube further defines one or more apertures therein, the one or more apertures configured to allow a fluid and/or a substance to pass therethrough from a first balloon catheter lumen defined within the balloon catheter tube. In yet an additional embodiment, the balloon catheter tube further defines a distal tube aperture in communication with a second balloon catheter lumen, wherein at least a portion of the thrombus from within the lumen of the mammalian vessel can enter second balloon catheter lumen through the distal tube aperture when suction is applied through the second balloon catheter lumen to remove at least a portion of the thrombus.

In an exemplary embodiment of a thrombus removal system of the present disclosure, the balloon catheter tube is configured so that a fluid can be introduced through the first balloon catheter lumen, through the one or more apertures, and into the lumen of the mammalian vessel to flush the lumen of the mammalian vessel. In an additional embodiment, the system is configured to introduce one or more disruptive oscillations through one or more of the balloon catheter and a portion of the second occlusion element and into the lumen of the mammalian vessel, wherein the one or more disruptive oscillations capable of disrupting at least a portion of the thrombus. In yet an additional embodiment, the thrombus removal system further comprises a substance source in communication with a first balloon catheter lumen defined within the balloon catheter tube, the substance source capable of introducing one or more chemical agents and/or or a fluid from the substance source, through the first balloon catheter lumen, through one or more apertures defined within the balloon catheter tube, and into the lumen of the mammalian vessel. In another embodiment, the thrombus removal system further comprises a suction source in communication with a second balloon catheter lumen defined within the balloon catheter tube, the suction source capable of removing fluid and/or a particulate from the lumen of the mammalian vessel during operation of the suction source.

In an exemplary embodiment of a thrombus removal system of the present disclosure, the thrombus removal system comprises a guidewire having a distal end, the guidewire configured to puncture a thrombus positioned within a lumen of a mammalian vessel, a balloon catheter comprising a balloon catheter tube and a first balloon coupled thereto, the first balloon capable of inflation within a lumen of a mammalian vessel to substantially or completely occlude the lumen of the mammalian vessel, and a second occlusion element configured to at least substantially occlude the lumen of the mammalian vessel, the second occlusion element selected from the group consisting of (i) an umbrella catheter comprising an umbrella catheter tube and an umbrella positioned at least partially within the umbrella catheter tube when in a compressed configuration and positioned external to the umbrella catheter tube when in a deployed configuration, wherein the umbrella is configured to at least substantially occlude the lumen of the mammalian vessel when in the deployed configuration, and (ii) a second balloon coupled to the balloon catheter tube, the second balloon capable of inflation within the lumen of the mammalian vessel to substantially or completely occlude the lumen of the mammalian vessel, the thrombus removal system configured to disrupt and/or dissolve and remove at least a portion of the thrombus from within the lumen of the mammalian vessel by way introducing one or more chemical agents and/or one or more disruptive oscillations into the lumen of the vessel, the one or more chemical agents and/or one or more disruptive oscillations capable of disrupting and/or dissolving at least a portion of the thrombus.

BRIEF DESCRIPTION OF THE DRAWINGS

The above mentioned embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein:

FIGS. 1D and 2A show a deployed umbrella of the umbrella catheter shown in FIG. 1C, according to an embodiment of the present disclosure;

FIG. 2B shows the use of a chemical agent by way of a thrombus removal system within a mammalian vessel, according to an embodiment of the present disclosure;

FIG. 2C shows the disruption and/or dissolution of at least part of a thrombus from the use of a chemical agent by way of a thrombus removal system within a mammalian vessel, according to an embodiment of the present disclosure;

FIG. 3A shows a deployed umbrella of the umbrella catheter shown in FIG. 1C, according to an embodiment of the present disclosure;

FIG. 3B shows the use of disruptive oscillations by way of a thrombus removal system within a mammalian vessel, according to an embodiment of the present disclosure;

FIG. 3C shows the disruption of at least part of a thrombus from the use of disruptive oscillations by way of a thrombus removal system within a mammalian vessel, according to an embodiment of the present disclosure;

FIG. 4A shows portions of an exemplary thrombus removal system positioned within a mammalian vessel with a partially deflated balloon, according to an embodiment of the present disclosure;

FIG. 4B shows portions of an exemplary thrombus removal system positioned within a mammalian vessel with an inverted umbrella, according to an embodiment of the present disclosure;

FIG. 4C shows portions of an exemplary thrombus removal system positioned within a mammalian vessel with some or all of the umbrella positioned within the balloon catheter, according to an embodiment of the present disclosure;

FIG. 7A shows a balloon catheter having two balloons positioned within a thrombus within a mammalian vessel, according to an embodiment of the present disclosure;

FIG. 7B shows the use of a chemical agent by way of a thrombus removal system within a mammalian vessel, according to an embodiment of the present disclosure;

FIG. 7C shows the disruption and/or dissolution of at least part of a thrombus from the use of a chemical agent by way of a thrombus removal system within a mammalian vessel, according to an embodiment of the present disclosure;

FIG. 8A shows a balloon catheter having two balloons positioned within a thrombus within a mammalian vessel, according to an embodiment of the present disclosure;

FIG. 8B shows the use of disruptive oscillations by way of a thrombus removal system within a mammalian vessel, according to an embodiment of the present disclosure;

FIG. 8C shows the disruption of at least part of a thrombus from the use of disruptive oscillations by way of a thrombus removal system within a mammalian vessel, according to an embodiment of the present disclosure;

FIG. 9A shows portions of an exemplary thrombus removal system positioned within a mammalian vessel with partially deflated balloons, according to an embodiment of the present disclosure;

FIG. 9B shows portions of an exemplary thrombus removal system positioned within a mammalian vessel with fully deflated balloons, according to an embodiment of the present disclosure;

Like reference numerals indicate the same or similar parts throughout the several figures.

Figure 1A:
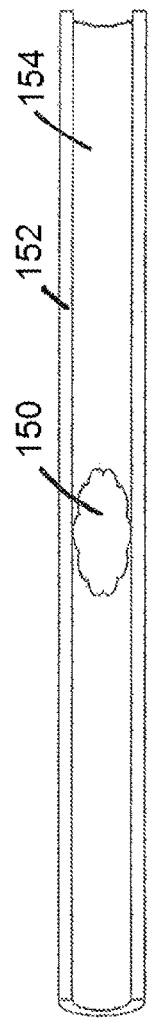
FIG. 1A shows a mammalian vessel with a thrombus positioned therein, according to an embodiment of the present disclosure.

An overview of the features, functions and/or configuration of the components depicted in the various figures will now be presented. It should be appreciated that not all of the features of the components of the figures are necessarily described. Some of these non-discussed features, such as various couplers, etc., as well as discussed features are inherent from the figures. Other non discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1B:
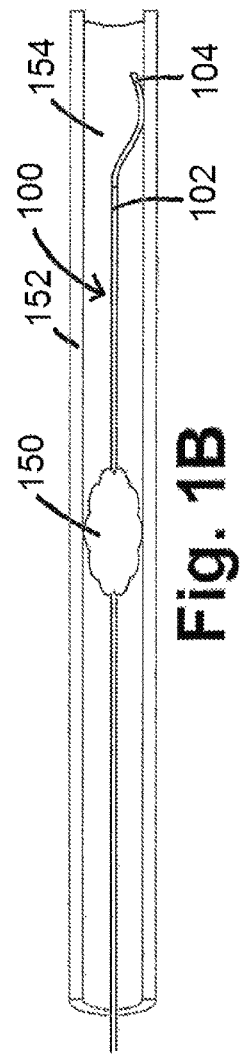
FIG. 1B shows at a guidewire positioned within a thrombus within a mammalian vessel, according to an embodiment of the present disclosure.
Figure 1C:
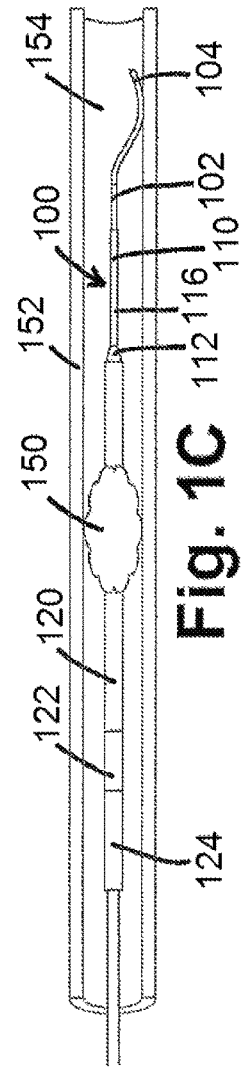
FIG. 1C shows an umbrella catheter and a balloon catheter positioned within a thrombus within a mammalian vessel, according to an embodiment of the present disclosure.
Figure 1D:
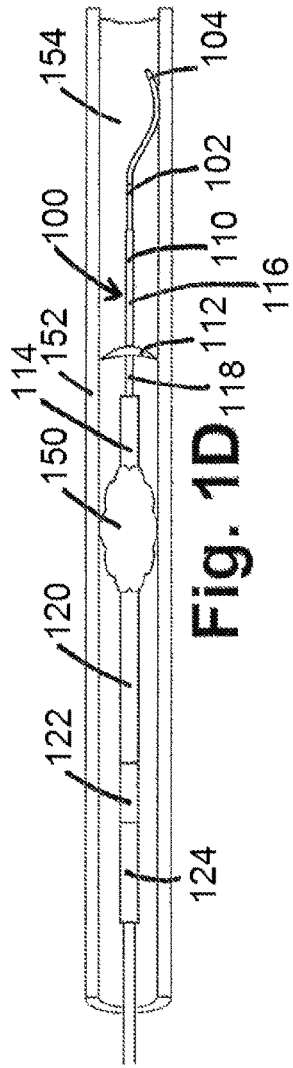

An exemplary embodiment of a thrombus removal system of the present disclosure is shown in FIGS. 1B-1D. As shown in FIG. 1B, at least part of a thrombus removal system 100 may be used to penetrate a thrombus 150 (shown alone within a mammalian vessel 152 in FIG. 1A) to facilitate removal of thrombus 150 from a lumen 154 of mammalian vessel 152. A guidewire 102, which may or may not be considered part of a thrombus removal system 100 (depending on the embodiment referenced), may be used to pierce thrombus 150 so that part of guidewire 102 appears proximal to, within, and distal to, thrombus 150. After piercing thrombus 150, guidewire 102 may be advanced so that a distal end 104 of guidewire 102 is distal to thrombus 150 as shown in FIGS. 1B-1D. For purposes of depicting use of guidewire 102 and/or other components of thrombus removal system 100, FIGS. 1A-4C show entry of guidewire 102 and/or other components of thrombus removal system 100 from the left side of mammalian vessel 152.

After insertion of guidewire 102 through thrombus 150, an umbrella catheter 110 (an exemplary component/device of a thrombus removal system 100 of the present disclosure) may be inserted over guidewire 102 so that part of umbrella catheter 110 is positioned proximal to, within, and distal to, thrombus 150, as shown in FIG. 1C. In addition, and also as shown in FIG. 1C, a balloon catheter 120 (another exemplary component/device of thrombus removal system 100 of the present disclosure) may be inserted over umbrella catheter 110 so that part of balloon catheter 120 (having a balloon 122 coupled to a balloon catheter tube 124) is positioned proximal to, within, and distal to, thrombus 150.

After umbrella catheter 110 (and potentially after balloon catheter 120) has/have been positioned, an umbrella 112 of umbrella catheter 110, may be deployed as shown in FIG. 1D, Deployment of umbrella 112 may be performed by, for example, retracting part of umbrella catheter 110, which itself comprises an umbrella catheter tube 116, opposite the initial direction of insertion of umbrella catheter into lumen 154 of vessel 152 so that umbrella 112 may deploy within lumen 154 of vessel 152. For example, a tube 114 of umbrella catheter 110, as shown in FIG. 1D, that initially housed some or all of umbrella 112 therein, may be retracted so that umbrella 112 may expand (which may be, for example, autoexpansion to an open configuration from a compressed configuration within tube 114). In at least another embodiment, advancement of a shaft 118 of umbrella catheter 110, as shown in FIG. 1D, may be performed to push umbrella 112 out of umbrella catheter 110 so that umbrella 112 can deploy within lumen 154 of vessel 152. Umbrella 112, in at least one embodiment, may comprise a mesh, fabric, or other material capable of allowing blood and/or other fluids within lumen 152 to pass therethrough, but preventing some or all of thrombus 150 from passing therethrough as thrombus 150 is disrupted/fractioned from the use of at least part of an exemplary thrombus removal system 100 of the present disclosure. In another embodiment, umbrella 112 may comprise a material that substantially or completely prevents any fluid or material within lumen 154 of vessel 152 from passing therethrough, including portions of thrombus 150.

After at least part of thrombus removal system 100 has been positioned within a vessel 152 (as shown in FIG. 1D), thrombus removal system 100 may be used to, for example, chemically and/or physically remove some or all of thrombus 150. In at least one embodiment of a chemical removal of some or all of thrombus 150 of the present disclosure, at least part of thrombus removal system 100 may be positioned within a thrombus 150 at a desired position (as shown in FIG. 1D and described above and as reproduced in FIG. 2A for convenience), whereby thrombus removal system 100 may be used to introduce one or more chemical agents 200 (depicted as squares within FIG. 2B) local to thrombus 150. Exemplary chemical agents 200 capable of disruption and/or dissolution of at least part of thrombus 150 may include, but are not limited to, one or more tissue plasminogen activators, plasmin, or thrombin, for example. So to avoid undesired exposure of vessel 152 of chemical agents 200 proximal to balloon 122 of balloon catheter 120, balloon 122 may be inflated, as shown in FIG. 2B. In addition, and to avoid undesired exposure of vessel 152 of chemical agents 200 and/or portions of thrombus 150 distal to umbrella 112 of umbrella catheter 110, umbrella 112 may be deployed as shown in FIGS. 2A-2C. Deployment of said umbrella 112, as referenced herein, operates to prevent portions of thrombus 150 from entering the blood stream and potentially forming a damaging, and potentially fatal, clot elsewhere in the body. Chemical agents 200 may be introduced through one or more apertures 202 defined within balloon catheter 120, so that chemical agents 200 from an agent source (not shown) can be introduced through a first lumen 204 of balloon catheter 120, out of aperture(s) 202, and into a lumen 154 of vessel 152. Over time, and as shown in FIG. 2C, chemical agents 200 may disrupt and/or dissolve at least part of thrombus 150, so that thrombus fragments 250 (depicted as circles within FIG. 2C) can break away from thrombus 150 and enter into a second lumen 206 of balloon catheter 120 by way of distal aperture 208. Removal of thrombus fragments 250 may occur via suction through distal aperture 208 of balloon catheter 120, so that thrombus fragments 250 may enter distal aperture 208 as indicated by the arrows shown in FIG. 2C.

In at least one embodiment, and to maintain at least a desired amount of fluid local to the treatment area, saline or another biologically compatible fluid may be introduced through aperture(s) 202, whereby said fluid may also help to flush the treatment area so that a desired amount or level of thrombus fragments 250 are removed from the lumen 154 of mammalian vessel 152.

In at least one embodiment of a physical removal of some or all of thrombus 150 of the present disclosure, at least part of thrombus removal system 100 may be positioned within a thrombus 150 at a desired position (as shown in FIG. 1D and described above and as reproduced in FIG. 3A for convenience), whereby thrombus removal system 100 may be used to introduce disruptive oscillations 300 therethrough (depicted as curved lines within FIG. 3B) local to thrombus 150. Disruptive oscillations 300 may be introduced via ultrasound or one or more other types of physical movement (side-to-side, back-and-forth, and/or in another direction) to increase the shear stress of thrombus 150 to disrupt thrombus 150 and cause portions of thrombus 150 to break away. So to avoid undesired exposure of vessel 152 proximal to balloon 122 of balloon catheter 120 to thrombus fragments 250, balloon 122 may be inflated, as shown in FIG. 3B. In addition, and to avoid undesired exposure of vessel 152 to portions of thrombus 150 distal to umbrella 112 of umbrella catheter 110, umbrella 112 may be deployed as shown in FIGS. 3A-3C. Over time, and as shown in FIG. 3C, disruptive oscillations 300 may disrupt thrombus 150, so that thrombus fragments 250 (depicted as circles within FIG. 3C) can break away from thrombus 150 and enter into a second lumen 206 of balloon catheter 120 by way of distal aperture 208. Removal of thrombus fragments 250 may occur via suction through distal aperture 208 of balloon catheter 120, so that thrombus fragments 250 may enter distal aperture 208 as indicated by the arrows shown in FIG. 3C. In at least one embodiment, and to maintain at least a desired amount of fluid local to the treatment area, saline or another biologically compatible fluid may be introduced through aperture(s) 202, whereby said fluid may also help to flush the treatment area so that a desired amount or level of thrombus fragments 250 are removed from the lumen 154 of mammalian vessel 152.

Removal of a thrombus removal system 100 of the present disclosure from a lumen 154 of a vessel 152 is shown in FIGS. 4A-4C. As shown in FIGS. 4A and 4B, balloon 122 is deflated (shown as partially deflated in FIG. 4A and completely deflated in FIG. 4B) to unsecure thrombus removal system 100 from vessel 152. Pull-back of one or more components of thrombus removal system 100 then causes the deployed umbrella 112 to invert (as shown in the change of orientation from FIG. 4A to FIG. 4B), and further pulling of umbrella catheter 110 back causes umbrella 112 to fit at least partially within distal aperture 208 to facilitate removal of thrombus removal system 100 from the lumen 154 of mammalian vessel 152.

Figure 5:
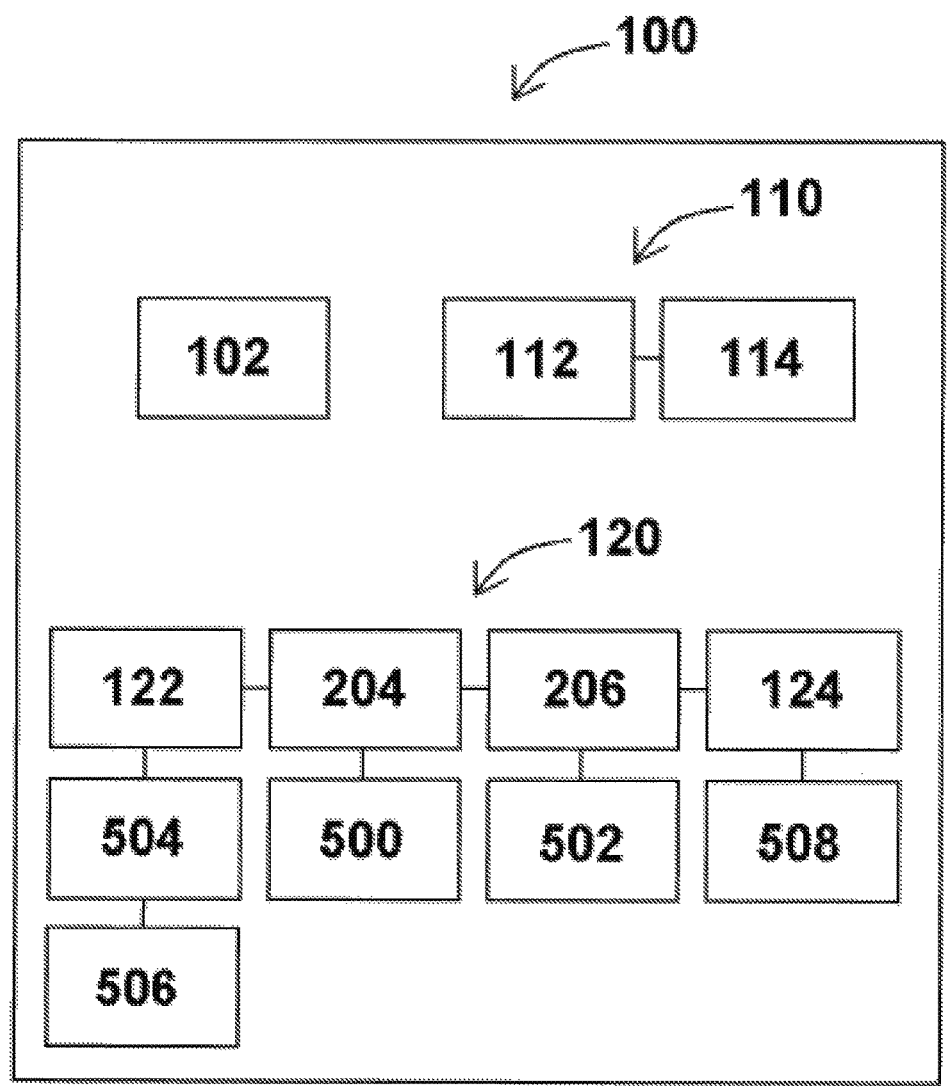
FIG. 5 shows a block diagram of various components of an exemplary thrombus removal system, according to an embodiment of the present disclosure.

FIG. 5 shows a block diagram of various components of an exemplary thrombus removal system 100 of the present disclosure. As shown in FIG. 5, an exemplary thrombus removal system 100 of the present disclosure may comprise a guidewire 102, an umbrella catheter 110 comprising an umbrella 112 and an umbrella catheter tube 114, and a balloon catheter 120 comprising a balloon 122 and a balloon catheter tube 124. Balloon catheter 120 may define a first lumen 204 therethrough, whereby one or more chemicals and/or a fluid from a substance source 500 can be provided from substance source 500, through the first lumen 204, through one or more apertures 202 defined within balloon catheter tube 124, and into a lumen 154 of a mammalian vessel 152. Balloon catheter 120 may also define a second lumen 206 therethrough, whereby suction from a suction source 502 may be provided through second lumen 206 into lumen 154 of mammalian vessel 152 to remove fluid and/or particulates through distal aperture 208. Balloon catheter 120 may further define a third lumen 504 therethrough, whereby an inflation/deflation source 506 in communication therewith is operable to inflate and/or deflate balloon 122 that is also in communication with third lumen 504. Further, and in at least one embodiment, an oscillator 508 (such as an ultrasound apparatus) may be in communication with one or more components of balloon catheter 120 to introduce disruptive oscillations into a lumen 154 of a mammalian vessel 152.

Figure 6:
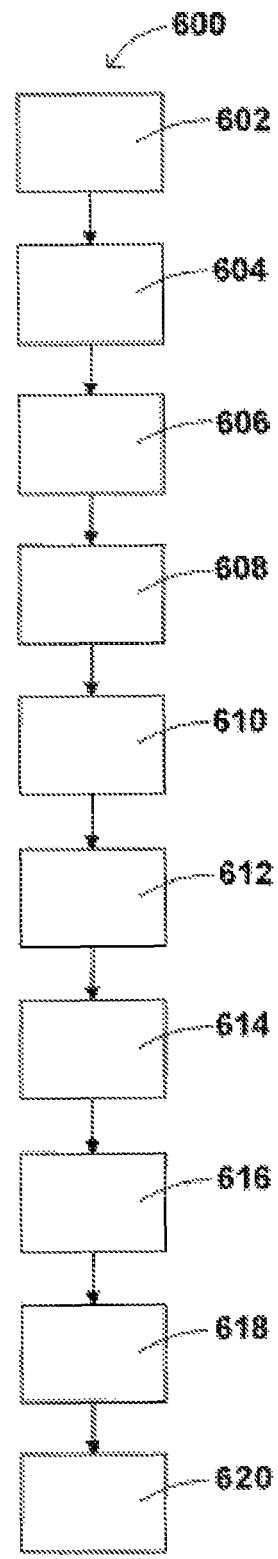
FIG. 6 shows steps of an exemplary method for using an exemplary thrombus removal system to remove a thrombus, according to an embodiment of the present disclosure.

As generally referenced above and as shown in the method step diagram of FIG. 6, an exemplary embodiment of a method of removing a thrombus from a lumen 154 of a mammalian vessel 152 is provided herein. In at least one embodiment of a method 600 of the present disclosure, method 600 comprises the steps of inserting a guidewire 102 into a lumen 154 of a mammalian vessel 152 through a thrombus 150 present therein (an exemplary guidewire insertion step 602), inserting an umbrella catheter 110 through the thrombus 150 around at least part of the guidewire 102 (an exemplary umbrella catheter insertion step 604), and inserting a balloon catheter 120 through the thrombus 150 around at least part of the umbrella catheter 110 (an exemplary balloon catheter insertion step 606). An exemplary method 600 of the present disclosure further comprises the steps of deploying an umbrella 112 of the umbrella catheter 110 to at least substantially occlude the lumen 154 of the mammalian vessel 152 distal to the thrombus 150 or to at least substantially prevent a portion of the thrombus 150 from passing through the umbrella 112 (an exemplary umbrella deployment step 608), inflating a balloon 122 of the balloon catheter 120 to at least substantially occlude the lumen 154 of the mammalian vessel 152 proximal to the thrombus 150 (an exemplary balloon inflation step 610), operating one or more of the umbrella catheter 110 and/or the balloon catheter 120 to disrupt and/or dissolve the thrombus 150 (an exemplary operation step 612), and applying suction through the balloon catheter 120 to remove at least part of the disrupted thrombus 150 from the lumen 154 of the mammalian vessel 152 (an exemplary thrombus removal step 614).

In at least one embodiment of method 600 of the present disclosure, operation step 612 comprises operating the balloon catheter 120 to introduce one or more chemical agents 200 through the balloon catheter 120 into the lumen 154 of the mammalian vessel 152 to disrupt and/or dissolve the thrombus 150. In at least another embodiment, operation step 612 comprises operating one or more of the umbrella catheter 110 and/or the balloon catheter 120 to introduce one or more disruptive oscillations therethrough to disrupt the thrombus 150.

In at least one embodiment of a method 600 of the present disclosure, method 600 further comprises the steps of deflating the balloon 122 (an exemplary balloon deflation step 616) and inverting the umbrella 112 (an exemplary umbrella inversion step 618) so that the umbrella 112 can be positioned at least partially within a distal aperture 208 of the balloon catheter 120, and removing the guidewire 102, the umbrella catheter 110, and the balloon catheter 120 from the lumen 154 of the mammalian vessel 152 (an exemplary system removal step 620).

At least another embodiment of a thrombus removal system 100 of the present disclosure is shown in FIGS. 7A-7C. As shown in FIG. 7A, a guidewire 102 is positioned through a thrombus 150, and a balloon catheter 120 is positioned around at least part of guidewire 102. As shown in FIG. 7A, balloon catheter 120 comprises a first balloon 122 positioned along balloon catheter 120 proximal to thrombus 150, and further comprises a second balloon 700 positioned along balloon catheter 120 distal to thrombus 150. In such an embodiment, balloon catheter 120 may define a lumen 504 in communication with an inflation/deflation source 506, whereby lumen 504 is in communication with first balloon 122 and second balloon 700 to inflate and/or deflate said balloons 122, 700. In at least another embodiment, an additional lumen 702 may be defined within balloon catheter 120, whereby lumen 504 is in communication with first balloon 122 and the additional lumen 702 is in communication with second balloon 700, so that an inflation/deflation source 506 in communication with lumens 504, 702 may inflate and/or deflate balloons 122, 700 separately.

In at least another embodiment of a chemical removal of some or all of thrombus 150 of the present disclosure, at least part of thrombus removal system 100 may be positioned within a thrombus 150 at a desired position (as shown in FIG. 7A), whereby thrombus removal system 100 may be used to introduce one or more chemical agents 200 capable of disruption and/or dissolution of at least part of thrombus 150 (depicted as squares within FIG. 7B) local to thrombus 150. So to avoid undesired exposure of vessel 152 of chemical agents 200 proximal to first balloon 122 of balloon catheter 120, first balloon 122 may be inflated, as shown in FIGS. 7B and 7C. In addition, and to avoid undesired exposure of vessel 152 of chemical agents 200 and/or portions of thrombus 150 distal to second balloon 700, second balloon 700 may also be inflated, as shown in FIGS. 7B and 7C. Chemical agents 200 may be introduced through one or more apertures 202 defined within balloon catheter 120, so that chemical agents 200 from an agent source (not shown) can be introduced through a lumen 204 of balloon catheter 120, out of aperture(s) 202, and into a lumen 154 of vessel 152. Over time, and as shown in FIG. 7C, chemical agents 200 may disrupt and/or dissolve at least part of thrombus 150, so that thrombus fragments 250 (depicted as circles within FIG. 7C) can break away from thrombus 150 and enter into a second lumen 206 of balloon catheter 120 by way of aperture 208. Removal of thrombus fragments 250 may occur via suction through aperture 208 of balloon catheter 120, so that thrombus fragments 250 may enter aperture 208 as indicated by the arrows shown in FIG. 7C.

As generally referenced herein, an "occlusion element" may refer to a balloon catheter 120 with one or more balloons 122, 700, or may refer to an umbrella catheter 110 with one or more umbrellas 112. For example, an exemplary embodiment of a thrombus removal system 100 of the present disclosure may comprise a balloon catheter 120 with a first balloon 122 and an occlusion element, with the occlusion element being either an umbrella catheter 110 with one or more umbrellas 112 (as shown in FIGS. 2B and 2C, for example), or a balloon catheter 120 with a second balloon 700 (as shown in FIGS. 7B and 7C, for example).

In at least another embodiment of a physical removal of some or all of thrombus 150 of the present disclosure, at least part of thrombus removal system 100 may be positioned within a thrombus 150 at a desired position (as shown in FIG. 8A), whereby thrombus removal system 100 may be used to introduce disruptive oscillations 300 therethrough (depicted as curved lines within FIG. 8B) local to thrombus 150. Disruptive oscillations 300 may be introduced via ultrasound or one or more other types of physical movement (side-to-side, back-and-forth, and/or in another direction) to increase the shear stress of thrombus 150 to disrupt thrombus 150 and cause portions of thrombus 150 to break away. So to avoid undesired exposure of vessel 152 proximal to first balloon 122 of balloon catheter 120 to thrombus fragments 250, first balloon 122 may be inflated, as shown in FIGS. 8B and 8C. In addition, and to avoid undesired exposure of vessel 152 to portions of thrombus 150 distal to second balloon 700, second balloon 700 may also be inflated, as shown in FIGS. 8B and 8C. Over time, and as shown in FIG. 8C, disruptive oscillations 300 may disrupt thrombus 150, so that thrombus fragments 250 (depicted as circles within FIG. 8C) can break away from thrombus 150 and enter into a second lumen 206 of balloon catheter 120 by way of aperture 208. Removal of thrombus fragments 250 may occur via suction through aperture 208 of balloon catheter 120, so that thrombus fragments 250 may enter aperture 208 as indicated by the arrows shown in FIG. 8C. In at least one embodiment, and to maintain at least a desired amount of fluid local to the treatment area, saline or another biologically compatible fluid may be introduced through aperture(s) 202, whereby said fluid may also help to flush the treatment area so that a desired amount or level of thrombus fragments 250 are removed from the lumen 154 of mammalian vessel 152.

Removal of an exemplary thrombus removal system 100 of the present disclosure from a lumen 154 of a vessel 152 is shown in FIGS. 9A and 9B. As shown in FIGS. 9A and 9B, balloons 122, 700 are deflated (shown as partially deflated in FIG. 9A and completely deflated in FIG. 9B) to unsecure thrombus removal system 100 from vessel 152 to facilitate removal of thrombus removal system 100 from the lumen 154 of mammalian vessel 152.

Figure 10:
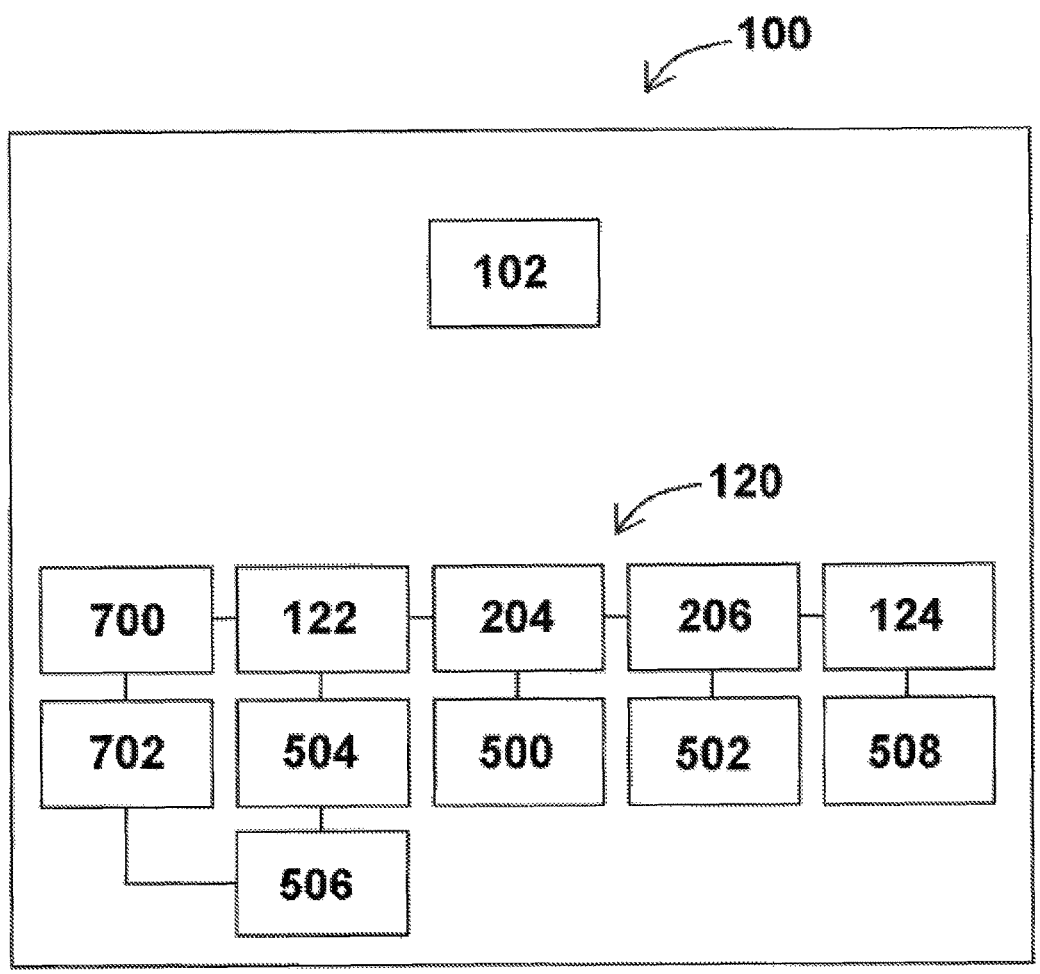
FIG. 10 shows a block diagram of various components of an exemplary thrombus removal system, according to an embodiment of the present disclosure.

FIG. 10 shows a block diagram of various components of another exemplary thrombus removal system 100 of the present disclosure. As shown in FIG. 10, an exemplary thrombus removal system 100 of the present disclosure may comprise a guidewire 102 and a balloon catheter 120 comprising a first balloon 122, a second balloon 700, and a balloon catheter tube 124. Balloon catheter 120 may define a first lumen 204 therethrough, whereby one or more chemicals and/or a fluid from a substance source 500 can be provided from substance source 500, through the first lumen 204, through one or more apertures 202 defined within balloon catheter tube 124, and into a lumen 154 of a mammalian vessel 152. Balloon catheter 120 may also define a second lumen 206 therethrough, whereby suction from a suction source 502 may be provided through second lumen 206 into lumen 154 of mammalian vessel 152 to remove fluid and/or particulates through distal aperture 208. Balloon catheter 120 may further define a third lumen 504 therethrough, whereby an inflation/deflation source 506 in communication therewith is operable to inflate and/or deflate first balloon 122 that is also in communication with third lumen 504. Balloon catheter 120 may further define a fourth lumen 702 therethrough, whereby an inflation/deflation source 506 in communication therewith is operable to inflate and/or deflate second balloon 700 that is also in communication with fourth lumen 702. Further, and in at least one embodiment, an oscillator 508 (such as an ultrasound apparatus) may be in communication with one or more components of balloon catheter 120 to introduce disruptive oscillations into a lumen 154 of a mammalian vessel 152.

Figure 11:
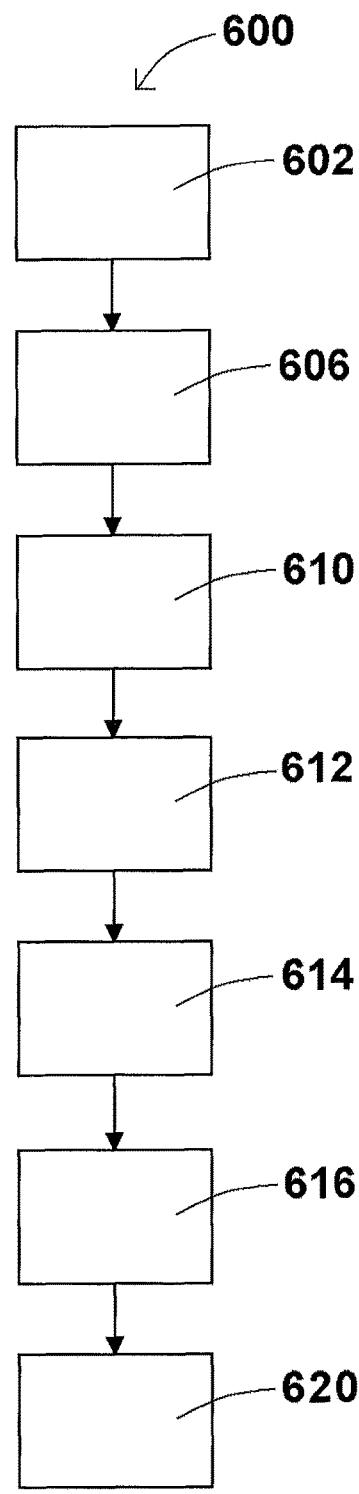
FIG. 11 shows steps of an exemplary method for using an exemplary thrombus removal system to remove a thrombus, according to an embodiment of the present disclosure.

As generally referenced above and as shown in the method step diagram of FIG. 11, another exemplary embodiment of a method of removing a thrombus from a lumen 154 of a mammalian vessel 152 is provided herein. In at least one embodiment of a method 600 of the present disclosure, method 600 comprises an exemplary guidewire insertion step 602, an exemplary balloon catheter insertion step 606, and the step of inflating balloons 122, 700 of the balloon catheter 120 to at least substantially occlude the lumen 154 of the mammalian vessel 152 proximal and distal to the thrombus 150 (another exemplary balloon inflation step 610). In at least one embodiment of method 600 of the present disclosure, method 600 further comprises operating the balloon catheter 120 to disrupt and/or dissolve the thrombus 150 (another exemplary operation step 612) and an exemplary thrombus removal step 614.

In at least one embodiment of method 600 of the present disclosure, operation step 612 comprises operating the balloon catheter 120 to introduce one or more chemical agents 200 through the balloon catheter 120 into the lumen 154 of the mammalian vessel 152 to disrupt and/or dissolve the thrombus 150. In at least another embodiment, operation step 612 comprises operating the balloon catheter 120 to introduce one or more disruptive oscillations therethrough to disrupt the thrombus 150.

In at least one embodiment of a method 600 of the present disclosure, method 600 further comprises the steps of deflating balloons 122, 700 (another exemplary balloon deflation step 616) and removing the guidewire 102 and the balloon catheter 120 from the lumen 154 of the mammalian vessel 152 (another exemplary system removal step 620).

Various thrombus removal systems 100 of the present disclosure may comprise components known in the catheter arts, such as biologically-compatible plastics, rubber, stainless steel, and the like.

While various embodiments of thrombus removal systems and devices and methods of using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A thrombus removal system, comprising:
a balloon catheter comprising a balloon catheter tube, a first balloon coupled thereto, and defining a first lumen therethrough terminating at a distal tube aperture at a distal end of the balloon catheter and a second lumen therethrough terminating at one or more apertures defined within the balloon catheter tube at a location outside of the first balloon;
the first balloon capable of inflation within a lumen of a mammalian vessel to substantially or completely occlude the lumen of the mammalian vessel proximal to a thrombus positioned within the lumen of the mammalian vessel;
a second occlusion element comprising an umbrella catheter comprising an umbrella coupled to a catheter, the umbrella moveable between a compressed configuration and a first deployed configuration;
wherein the umbrella comprises an inverted second deployed configuration and wherein the umbrella is configured so that proximal movement of the umbrella catheter within the lumen of a mammalian vessel is itself sufficient to invert the umbrella to the second deployed configuration and wherein the umbrella is configured to allow fluid to pass therethrough but prevent at least a portion of the thrombus from passing therethrough when in the first deployed configuration;
wherein the balloon catheter is insertable around at least a portion of the second occlusion element; and
the thrombus removal system is configured to disrupt and/or dissolve at least a portion of the thrombus and remove at least a portion of the thrombus using suction through the distal tube aperture of the balloon catheter in operation when the first balloon is positioned proximal to thrombus and when the second occlusion element is positioned distal to the thrombus.

2. The thrombus removal system of claim 1, wherein the first balloon is capable of inflation and deflation by way of an inflation/deflation lumen defined within the balloon catheter tube.

3. The thrombus removal system of claim 1, wherein the first balloon is capable of inflation and deflation by way of at least one inflation/deflation lumen defined within the balloon catheter tube.

4. The thrombus removal system of claim 3, wherein when the first balloon is positioned proximal to the thrombus and inflated to at least substantially occlude the lumen of the mammalian vessel and wherein when the umbrella is positioned distal to the thrombus and in the first deployed configuration operation of the balloon catheter can disrupt and/or dissolve the thrombus, and use of suction through the first lumen of the balloon catheter can facilitate removal of at least part of the disrupted thrombus from the lumen of the mammalian vessel.

5. The thrombus removal system of claim 1, wherein the system is configured to introduce one or more chemical agents into the lumen of the mammalian vessel, the one or more chemical agents capable of disrupting and/or dissolving at least a portion of the thrombus.

6. The thrombus removal system of claim 1, wherein the one or more apertures defined within the balloon catheter tube are configured to allow a fluid and/or a substance to pass therethrough from the second lumen defined within the balloon catheter.

7. The thrombus removal system of claim 6, wherein the balloon catheter tube is configured so that a fluid can be introduced through the first balloon catheter lumen, through the one or more apertures, and into the lumen of the mammalian vessel to flush the lumen of the mammalian vessel.

8. The thrombus removal system of claim 6, further comprising:
a substance source in communication with the second lumen defined within the balloon catheter tube, the substance source capable of introducing one or more chemical agents and/or a fluid from the substance source, through the second balloon catheter lumen, through the one or more apertures defined within the balloon catheter tube, and into the lumen of the mammalian vessel.

9. The thrombus removal system of claim 1, wherein the system is configured to introduce one or more disruptive oscillations through one or more of the balloon catheter and a portion of the second occlusion element and into the lumen of the mammalian vessel, wherein the one or more disruptive oscillations are capable of disrupting at least a portion of the thrombus.

10. The thrombus removal system of claim 1, further comprising:
a suction source in communication with the first balloon catheter lumen defined within the balloon catheter tube, the suction source capable of removing fluid and/or a particulate from the lumen of the mammalian vessel during operation of the suction source.

11. The thrombus removal system of claim 1, wherein a substance can be delivered through the second lumen and out of the one or more apertures into the lumen of the mammalian vessel to disrupt and/or dissolve at least part of the thrombus.

12. A thrombus removal system, comprising:
a guidewire having a distal end, the guidewire configured to puncture a thrombus positioned within a lumen of a mammalian vessel;
a balloon catheter comprising a balloon catheter tube, a first balloon coupled thereto, and defining a first lumen therethrough terminating at a distal tube aperture at a distal end of the balloon catheter and a second lumen therethrough terminating at one or more apertures defined within the balloon catheter tube, the first balloon capable of inflation within a lumen of a mammalian vessel to substantially or completely occlude the lumen of the mammalian vessel proximal to the thrombus, and the balloon catheter configured such that a fluid can be introduced through the second balloon catheter lumen, through the one or more apertures, and into the lumen of the mammalian vessel;
a second occlusion element comprising an umbrella catheter slidably disposed within the first lumen of the balloon catheter and extending through the distal tube aperture thereof, the umbrella catheter comprising an umbrella coupled with a catheter, the umbrella moveable between a compressed configuration and a first deployed configuration, wherein the umbrella is configured to invert to a second deployed configuration upon application of a proximal force, the second deployed configuration having an inverted orientation relative to the first deployed configuration that, upon retraction of the catheter of the umbrella catheter, can be positioned at least partially within the distal tube aperture of the balloon catheter, and wherein proximal movement of the umbrella catheter within the lumen of a mammalian vessel is itself sufficient to invert the umbrella to the second deployed configuration, wherein the umbrella is configured to allow fluid to pass therethrough but prevent at least a portion of the thrombus from passing therethrough when in the first deployed configuration; and
the balloon catheter is configured to fit around at least part of the umbrella catheter and the thrombus removal system configured to disrupt and/or dissolve at least a portion of the thrombus and remove at least a portion of the thrombus using suction through the distal tube aperture of the balloon catheter from within the lumen of the mammalian vessel in operation when the first balloon is positioned proximal to thrombus and when the second occlusion element is positioned distal to the thrombus by way of introducing one or more disruptive oscillations into the lumen of the vessel, the one or more disruptive oscillations capable of disrupting and/or dissolving at least a portion of the thrombus.

13. The thrombus removal system of claim 12, wherein at least part of the umbrella catheter is configured to fit around the guidewire.

14. The thrombus removal system of claim 12, wherein when the first balloon is positioned proximal to the thrombus and inflated to at least substantially occlude the lumen of the mammalian vessel and wherein when the umbrella is positioned distal to the thrombus, operation of one or more of the umbrella catheter and/or the balloon catheter can disrupt and/or dissolve the thrombus, and use of suction through the first lumen of the balloon catheter can facilitate removal of at least part of the disrupted thrombus from the lumen of the mammalian vessel.

15. The thrombus removal system of claim 12, wherein the second lumen of the balloon catheter is in fluid communication with an agent source comprising one or more chemical agents such that the one or more chemical agents can be introduced through the second lumen of the balloon catheter and into the lumen of the mammalian vessel, the one or more chemical agents capable of dilution of at least part of the thrombus.

16. A method of removing a thrombus from a lumen of a mammalian vessel, the method comprising the steps of:
inserting a guidewire into a lumen of a mammalian vessel through a thrombus present therein;
inserting an umbrella catheter through the thrombus around at least part of the guidewire, the umbrella catheter comprising an umbrella coupled with a catheter and a retractable tube slidably disposed over at least part of the catheter, the umbrella moveable between a compressed configuration and at least a first deployed configuration and the retractable tube configured to house some or all of the umbrella therein when the umbrella is in the compressed configuration, the umbrella configured to allow fluid to pass therethrough but prevent at least a portion of the thrombus from passing therethrough when in the first deployed configuration;
inserting a balloon catheter around at least part of the umbrella catheter, the balloon catheter defining a first lumen therethrough terminating at a distal aperture and a second lumen therethrough terminating at one or more apertures defined within the balloon catheter at a location outside of a first balloon coupled thereto;
deploying the umbrella of the umbrella catheter to the first deployed configuration by retracting the retractable tube to at least substantially prevent a portion of the thrombus from passing through the umbrella;
inflating a first balloon of the balloon catheter to at least substantially occlude the lumen of the mammalian vessel proximal to the thrombus;
operating one or more of the umbrella catheter and/or the balloon catheter to disrupt the thrombus by introducing one or more disruptive oscillations therethrough;
applying suction through the balloon catheter to remove at least part of the disrupted thrombus from the lumen of the mammalian vessel; and
moving the umbrella catheter proximally so that the umbrella inverts from the proximal movement of the umbrella catheter itself.

17. The method of claim 16, wherein the step of operating one or more of the umbrella catheter and/or the balloon catheter further comprises introducing one or more chemical agents through the balloon catheter into the lumen of the mammalian vessel to dissolve the thrombus.

18. The method of claim 16, further comprising the steps of:
deflating the first balloon and positioning the umbrella at least partially within a distal aperture of the balloon catheter; and
removing the guidewire, the umbrella catheter, and the balloon catheter from the lumen of the mammalian vessel.

* * * * *